United States Patent [19]

Byron et al.

[11] Patent Number: 5,492,688
[45] Date of Patent: *Feb. 20, 1996

[54] METERED DOSE INHALER FOMULATIONS WHICH INCLUDE THE OZONE-FRIENDLY PROPELLANT HFC 134A AND A PHARMACEUTICALLY ACCEPTABLE SUSPENDING, SOLUBILIZING, WETTING, EMULSIFYING OR LUBRICATING AGENT

[75] Inventors: Peter R. Byron; Frank E. Blondino, both of Richmond, Va.

[73] Assignees: The Center for Innovative Technology, Herndon; Virginia Commonwealth University, Richmond, both of Va.

[*] Notice: The term of this patent shall not extend beyond the expiration date of Pat. No. 5,190,029.

[21] Appl. No.: 217,012

[22] Filed: Mar. 23, 1994

Related U.S. Application Data

[63] Continuation of Ser. No. 54,625, Apr. 28, 1993, abandoned.
[51] Int. Cl.$^6$ ...................................................... A61K 9/12
[52] U.S. Cl. ................ 424/45; 424/46; 252/305; 514/958
[58] Field of Search ..................... 424/45, 43, 46; 514/958; 252/305

[56] References Cited

U.S. PATENT DOCUMENTS

| | | | |
|---|---|---|---|
| 4,174,295 | 11/1979 | Bargigia et al. | 424/45 |
| 4,945,119 | 7/1990 | Smits et al. | 252/182.15 |
| 5,190,029 | 3/1993 | Byron et al. | 424/45 |
| 5,202,110 | 4/1993 | Dalby et al. | 424/45 |

FOREIGN PATENT DOCUMENTS

| | | | |
|---|---|---|---|
| 0372777 | 6/1990 | European Pat. Off. | 424/45 |
| 04011 | 4/1991 | WIPO . | |

Primary Examiner—Thurman K. Page
Assistant Examiner—Raj Bawa
Attorney, Agent, or Firm—Whitham, Curtis, Whitham & McGinn

[57] ABSTRACT

Metered dose inhaler (MDI) formulations which utilize 1,1,1,2-tetrafluoroethane (HFC 134a) as the sole propellant are made practical by including a polar surfactant such as polyethylene glycol, diethylene glycol monoethyl ether, polyoxyethylene (20) sorbitan monolaurate, polyoxyethylene (20) sorbitan monooleate, propoxylated polyethylene glycol, and polyoxyethylene (4) lauryl ether for suspending, solubilizing, wetting and emulsifying the drug constituent and lubricating the valve components of the MDI.

7 Claims, No Drawings

METERED DOSE INHALER FOMULATIONS WHICH INCLUDE THE OZONE-FRIENDLY PROPELLANT HFC 134A AND A PHARMACEUTICALLY ACCEPTABLE SUSPENDING, SOLUBILIZING, WETTING, EMULSIFYING OR LUBRICATING AGENT

This is a continuation of application Ser. No. 08/054,625, filed Apr. 28, 1993, now abandoned.

DESCRIPTION

1. Field of the Invention

This invention is particularly related to drug formulations for use in a metered dose inhaler (MDI) which include 1,1,1,2-tetrafluoroethane (HFC 134a) as a propellant.

2. Description of the Prior Art

Chlorofluorocarbons (CFCs) have been used for many years in a wide variety of industries including refrigeration, air conditioning, polymer and foam blowing, etc. CFCs, and particularly blends of $CCl_3F$ (propellant 11), $CCl_2F_2$ (propellant 12), and $C_2Cl_2F_4$ (propellant 114), have been used extensively as propellants in drug formulations that are delivered to patients via an MDI. However, recent scientific evidence suggests that CFCs damage the Earth's ozone layer. Therefore, treaties amongst most of the industrialized world have called for a ban on CFC production and usage.

HFC 134a is the leading candidate for replacement of the ozone damaging CFC propellants. However, unlike industrial applications such as polymer and foam blowing, etc., substitution of a non-CFC propellant for the CFC propellants in MDI formulations is not straight forward. There are toxicity concerns as well as drug solubility and deliverability problems which must be addressed when substituting propellants in an MDI formulation. MDIs contain drugs which are dissolved or suspended as micronized particles, propellants in the form of liquified gases, and surface active compounds, or "surfactants", of a type and in a concentration suitable for suspension or dissolution of the drug. In some solution formulations, a co-solvent may be added to enhance drug dissolution, although this practice has the disadvantage of decreasing the fraction of the metered dose which may be inhaled. The surfactant is also included in the formulation to improve valve function by virtue of its lubricating properties. In order to achieve these objectives, the surfactant must be dissolved in sufficient concentrations. For example, in suspension systems, the surfactant is often incorporated in about 1/10 th the concentration of drug and the latter may typically vary from 0.02% to 5% weight in volume (w/v).

European Patent Application 0,372,777 of Riker Laboratories discloses MDI formulations which include HFC-134a, a surface active agent, and an adjuvant compound having a higher polarity than HFC-134a. The inclusion of a higher polarity compound in the formulation is said to be critical to the stability and performance of the MDI formulation. Exemplary compounds of "higher polarity than HFC 134a" according to European Patent Application 0,372,777 include ethanol, pentane, isopentane and neopentane. European Patent Application 0,372,777 lists a variety of surfactants which could be employed in the MDI formulations including sorbitan trioleate available under the trade name Span 85, sorbitan mono-oleate available under the trade name Span 80, sorbitan monolaurate available under the trade name Span 20, polyoxyethylene (20) sorbitan monolaurate available under the trade name Tween 20, polyoxyethylene (20) sorbitan mono-oleate available under the trade name Tween 80, lecithins derived from natural sources such as those available under the trade name Epikuron (particularly Epikuron 200), oleyl polyoxyethylene (2) ether available under the trade name Brij 92, stearyl polyoxyethylene (2) ether available under the trade name Brij 72, lauryl polyoxyethylene (4) ether available under the trade name Brij 30, oleyl polyoxyethylene (2) ether available under the trade name Genapol 0-020, block copolymers of oxyethylene and oxypropylene available under the trade name synperonic, oleic acid, synthetic lecithin, diethylene glycol dioleate, tetrahydrofurfuryl oleate, ethyl oleate, isopropyl myristate, glyceryl trioleate, glyceryl monolaurate, glyceryl monooleate, glyceryl monostearate, cetyl alcohols, stearyl alcohol, polyethylene glycol, and cetyl pyridinium chloride.

Having more than one propellant in an MDI formulation can present the manufacturer with production complexities as well as more severe regulatory hurdles. U.S. Pat. No. 5,182,097 to Byron et al. discloses that HFC 134a can be used as the sole propellant in an aerosol formulation if oleic acid is used as the surfactant. U.S. Pat. No. 5,126,123 to Johnson discloses the use of fluorocarbon surfactants in MDI formulations which contain HFC 134a as the sole propellant

SUMMARY OF THE INVENTION

It is an object of this invention to provide an aerosol formulation for use in an MDI which utilizes HFC 134a as the sole propellant and uses a polar surface active agent to aid in suspending, solubulizing, wetting, and emulsifying the micronized drug particles as well as lubricating the valve components of the MDI canister.

According to the invention, it has been discovered that a number of polar surface active agents dissolve appreciably in HFC-134a and, therefore, will be useful as suspending, wetting and lubricating agents or cosolvents in MDI formulations which include HFC-134a as the sole propellant.

DETAILED DESCRIPTION OF THE PREFERRED EMBODIMENTS OF THE INVENTION

Propellant 134a is a very poor solvent which fails to dissolve the commonly used surfactants sorbitan trioleate, sorbitan mono-oleate, lecithins and oleic acid in useful concentrations without the aid of a co-solvent. The vapor pressure, chemical structure, "poor solvency" and miscibility with other hydrophobic propellants like butane, have been believed by most investigators in the field to indicate that HFC 134a is extremely lipophilic. The commonly used MDI surfactants are all lipophilic themselves and are characterized by low HLB values.

It has been observed that HFC 134a is miscible in all proportions with 99.9% ethanol, which itself is a fairly poor solvent. This observation has led the inventors to conclude the assumption that HFC 134a is extremely lipophilic is completely incorrect.

In U.S. Pat. No. 5,126,123, Johnson resorted to using fluorocarbon surfactants as a possible means of ensuring dissolution in HFC 134a. However, the fluorocarbon surfactants, like many other surfactants, are likely to be irritating or toxic when presented by inhalation. Wang and Kowal have reviewed a list of surface active agents that are generally regarded as safe (GRAS) because they are included in parenteral products which are marketed in the United States. By investigating the solubilities of surfactants in HFC 134a, the inventors have discovered that a number of surprisingly polar surfactants dissolved appreciably in liquified HFC 134a.

Table 1 discloses the observed solubility of various surfactants/solubilizers (SAA; surface active agent) in HFC 134a, where time zero indicates the time of manufacture of the solution containing HFC 134a and SAA and time 24 hours indicates observations of the solution one day after manufacture.

TABLE 1

| Surfactant/ solubilizer (SAA) | Wt. of SAA (g) | Wt. of HFC134a (g) | Apparent solubility (% W/W) | Time = 0 hrs Temp = 20° C. | Time = 24 hrs Temp = 19° C. |
|---|---|---|---|---|---|
| •Macol SA 2 polyoxyethylene (2) stearyl ester | 0.009 | 75.510 | <<0.01 | no affect on the SAA | no change |
| •PEG 300 polyethylene glycol | 0.308 2.005 | 7.460 39.173 | 3.96 4.87 | clear solutions | slightly cloudy no change |
| •PEG 8000 polyethlyene glygol | 0.011 | 81.545 | <<0.01 | no affect on the SAA | no change |
| •Span 85 Sorbitan trioleate | 0.009 | 78.894 | <<0.01 | SAA remained as globule on bottom of container | no change |
| •oleic acid | 0.012 | 68.758 | <<0.02 | SAA present as smear on container wall | ring at liquid/ vapor interface |
| •Transcutol purified diethylene glycol monoethyl ether | 0.205 1.999 | 2.020 3.409 | 9.21 39.96 | appears miscible in all proportions clear solution | no change |
| •Tween 20 polyoxyethylene (20) sorbitan monolaurate | 0.048 0.049 | 44.860 42.458 | 0.11 0.12 | solubility >0.12% clear solution | no change |
| •Tween 80 polyoxyethylene (20) sorbitan monooleate | 0.010 0.019 | 46.803 75.309 | 0.02 0.03 | solubility >0.02% globules of SAA present | ring at liquid/ vapor (0.02%–0.03%) |
| •Aerosol-TO Dioctyl sodium sulfosuccinate | 0.009 | 73.413 | <<0.01 | no affect on the SAA | no change |
| •Antarox 31R1 Propoxylated polyethylene glycol | 0.206 1.007 | 13.397 26.941 | 1.54 3.74 | solubility greater than 3.74% | no change |
| •Arlacel 60 Sorbitan monostearate | 0.008 | 70.623 | <<0.01 | no affect on the SAA | no change |
| •BRIJ 30 polyoxy- ethylene (4) lauryl ether | 1.004 0.300 | 53.914 13.938 | 1.86 2.15 | clear cloudy solubility ~ 1.8% | no change |
| •Centrolex P Granular lecithin | 0.009 | 75.455 | <<0.01 | no affect on the SAA | no change |
| •Glycomul O Sorbitan Monooleate | 0.009 | 74.282 | <<0.01 | no affect on the SAA | no change |
| •Glycomul SOC Sorbitan sesquioleate | 0.010 | 73.324 | <<0.01 | no affect on the SAA | no change |

Table 1 shows that the polar surfactants polyethylene glycol, diethylene glycol monoethyl ether, polyoxyethylene (20) sorbitan monolaurate, polyoxyethylene (20) sorbitan monooleate, propoxylated polyethylene glycol, and polyoxyethylene (4) lauryl ether dissolved in HFC 134a. The observed dissolution of these polar compounds, which are commonly employed in aqueous solutions, in HFC 134a is surprising in view of the common perception that HFC 134a was highly lipophilic.

Because of their solubility in HFC 134a and their non-toxic character, the polar surfactants polyethylene glycol, diethylene glycol monoethyl ether, polyoxyethylene (20) sorbitan monolaurate, polyoxyethylene (20) sorbitan monooleate, propoxylated polyethylene glycol, and polyoxyethylene (4) lauryl ether, can be used as suspending, wetting and lubricating agents or as cosolvents in MDI formulations which will employ HFC 134a as a substitute propellant for the ozone damaging CFCs currently in use. The MDI formulations employing HFC 134a and the polar surfactant will be formulated in approximately the same proportions (e.g., greater than 90% propellant, less than 5% and most preferably less than 1% micronized drug (usually less than 5 microns in diameter), less than 5% surfactant and most preferably less than 2% surfactant), and will be prepared in the same manner as is currently done for CFCs (cold filling, pressure filling, etc.).

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. An aerosol formulation for use in a metered dose inhaler, consisting essentially of:

greater than 90% by weight of 1,1,1,2-tetrafluoroethane, said 1,1,1,2-tetrafluoroethane being the sole propellant and excipient which is not a surfactant in the aerosol formulation;

less than 5% by weight of micronized drug particles; and less than 5% by weight of a polar surfactant selected from the group consisting of polyethylene glycol 300, diethylene glycol monoethyl ether, polyoxyethylene 20 sorbitan monolaurate, polyoxyethylene 20 sorbitan monooleate, propoxylated polyethylene glycol, and polyoxyethylene 4 lauryl ether.

2. An aerosol formulation as recited in claim 1 wherein said polar surfactant is polyethylene glycol.

3. An aerosol formulation as recited in claim 1 wherein said polar surfactant is diethylene glycol monoethyl ether.

4. An aerosol formulation as recited in claim 1 wherein said polar surfactant is polyoxyethylene 20 sorbitan monolaurate.

5. An aerosol formulation as recited in claim 1 wherein said polar surfactant is polyoxyethylene 20 sorbitan monooleate.

6. An aerosol formulation as recited in claim 1 wherein said polar surfactant is propoxylated polyethylene glycol.

7. An aerosol formulation as recited in claim 1 wherein said polar surfactant is polyoxyethylene 4 lauryl ether.

* * * * *